United States Patent [19]
Mason

[11] Patent Number: 5,176,142
[45] Date of Patent: Jan. 5, 1993

[54] ENDOSCOPIC ULTRASOUND PROBE WITH TAKE-UP CABLE MECHANISM

[75] Inventor: Martin K. Mason, Andover, Mass.

[73] Assignee: Hewlett-Packard Company, Palo Alto, Calif.

[21] Appl. No.: 686,103

[22] Filed: Apr. 16, 1991

[51] Int. Cl.$^5$ .............................................. A61B 10/00
[52] U.S. Cl. .................................................. 128/662.06
[58] Field of Search ................... 128/660.1, 662.06; 73/633

[56] References Cited

U.S. PATENT DOCUMENTS

| | | | |
|---|---|---|---|
| 4,426,886 | 1/1984 | Finsterwald et al. | 73/633 |
| 4,543,960 | 10/1985 | Harui et al. | 128/662.06 |
| 4,869,257 | 9/1989 | Molnar et al. | 128/660.1 |
| 4,989,582 | 2/1991 | Sakiyama et al. | 128/358 |
| 4,996,974 | 3/1991 | Ciarlei | 128/138 |

OTHER PUBLICATIONS

Schlüter, M. "Transesophageal cross-sectional echocardiography with a phased array transducer system", Apr. 1982, Br Heart F, vol. 48: 67-72.
European Search Report, Jul. 24, 1992.

Primary Examiner—Francis Jaworski

[57] ABSTRACT

An endoscopic ultrasound probe has a rotatable transducer array for obtaining two-dimensional cross-sectional images of a subject along a variety of scan planes. The probe has take-up mechanism comprising a flexible cable assembly which electrically connects the array to remote ultrasound imaging system electronics. The flexible cable assembly is attached to the array within a first volume and is disposed in a second volume. As the array rotates, the take-up mechanism produces changes in the amount of the flexible cable within the second volume corresponding to changes in the amount of flexible cable within the first volume.

8 Claims, 3 Drawing Sheets

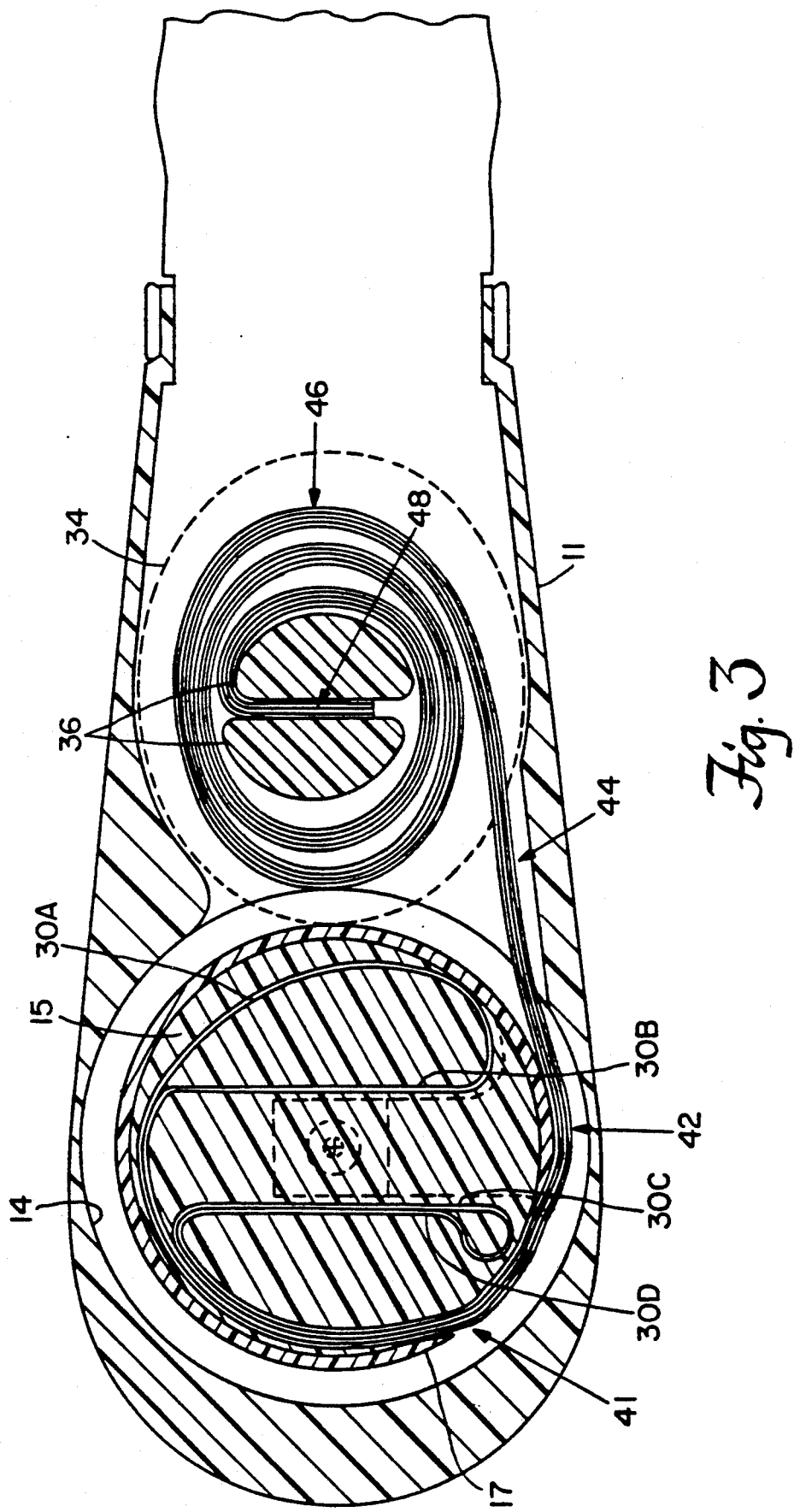

ENDOSCOPIC ULTRASOUND PROBE WITH TAKE-UP CABLE MECHANISM

BACKGROUND

Transesophageal echo cardiography is an established technique in the area of cardiac imaging and involves the insertion of an ultrasound probe into a subject's esophagus to scan the heart from inside the esophagus. An ultrasound probe may be formed by modifying an endoscope, whereby an ultrasound transducer array is affixed to the distal end of the endoscope. Typically, the probe is used with an ultrasound imaging system having electronics for remote excitation of the array to obtain cross-sectional images of the heart along a variety of scan planes as is well known. In "Transoesophageal Cross-Section Echocardiography With A Phased Array Transducer System" by Schluter et. al., an ultrasound probe having a rotatable array is suggested for obtaining an improved assessment of left ventricular morphology. Another ultrasound probe having a rotatable array is described in U.S. Pat. No. 4,543,960 to Harui et al.

SUMMARY OF THE INVENTION

In the Harui et al patent, an ultrasound scanhead has an array mounted on a rotatable base which is driven by a pulley. To rotate the array, control cables attached to the pulley are pulled, causing the pulley to rotate the base on which the array is mounted. The transducer elements are electrically connected a flexible cable which provides signals to a standard scan converter. To support rotation, the flexible cable is looped around the base to form a spiral cable assembly in a volume directly below the array.

The volume, however, requires a somewhat large diameter to accommodate the excess flexible cable in the spiral form. Since the cable is wrapped around the large diameter base, it has a large minimum diameter. The thickness of the cable, multiplied by the number of revolutions required to support rotation also contributes to the large diameter of the volume. Yet another factor is the space between adjacent revolutions of the spiral cable required to allow the spiral to become slack for certain rotational configurations. Thus, due to the large required diameter of the volume housing the array, the probe has a substantial transverse cross-sectional area which may lead to problems introducing the device into a subject's esophagus. Alternatively, the array size must be reduced which will adversely affect the resolution of the image.

The present invention avoids the problems of the aforementioned prior art through a unique cable take-up mechanism employed in an endoscopic ultrasound probe. In contrast to the prior art, the cable take-up mechanism is configured to minimize the diameter of the volume housing the array. As such, for a given array, the distal end of the probe has a smaller cross-sectional area and is easier to introduce into a subject's esophagus.

In accordance with this invention, the probe comprises a probe housing having a first volume and a second volume. A rotatable ultrasound transducer assembly is positioned in the first volume, and a take-up mechanism for a flexible cable, which cable is connected to the transducer assembly in the first volume and is disposed in the second volume, is located in the second volume. As the array rotates, the take-up mechanism produces changes in the amount of the flexible cable disposed within the second volume corresponding to changes in the amount of flexible cable within the first volume. The take-up mechanism allows the array to rotate freely, while ensuring that excess flexible cable is contained in the second volume. Thus, for a given array size, the first volume of the probe has a smaller diameter than the prior art, resulting in a smaller probe.

In a preferred embodiment, the present invention comprises a probe housing having an inner volume in its distal end and a rear volume adjacent to the inner volume. An ultrasound transducer array is supported on a rotatable structure within the inner volume. The array is formed of a plurality of transducer elements arranged in a plane and has a scan plane which is perpendicular to the elements of the array.

In accordance with this embodiment, a cable take-up mechanism comprises a flexible cable assembly which electrically connects the array to remote ultrasound imaging system electronics. Preferably, the flexible cable assembly comprises a plurality of integrally coupled flex cables, each having a plurality of signal lines printed thereon. One end of the flexible cable assembly is attached to the array and the other end is connected to a plurality of conductors which are linked to the remote electronics. A first portion of the flexible cable assembly extends from the array and may be fixed in a mass of acoustical damping material contained in the support structure. The first portion of the flexible cable assembly extends out of the support structure and forms a loop portion which wraps around the support structure within the inner volume. The loop portion extends into the rear volume which is adjacent to the inner volume. Within the rear volume, the flex cable assembly forms a spiral portion. The spiral portion has a sufficient number of revolutions of excess cable to support the rotation of the array. The innermost section of the spiral portion is preferably secured within the clamp and is linked to the remote electronics.

The cable take-up mechanism of this embodiment is configured to minimize the diameter of the inner volume. More specifically, the take-up mechanism is configured such that the spiral portion of the flex cable in the rear volume responds to changes in the loop portion within the inner volume. As the array rotates, the amount of cable forming the loop portion changes, producing corresponding changes in the amount of cable forming the spiral portion as well as the outer diameter of the spiral portion. Thus, the thickness of the loop portion of the flex cable assembly and the space required between revolutions to support rotation have a minimal effect on the diameter of the inner volume.

BRIEF DESCRIPTION OF THE DRAWINGS

In the enclosed drawings like reference characters refer to the same parts throughout the different views. The drawings are not necessarily to scale, emphasis instead being placed upon illustrating the principles of the invention.

FIG. 3 is a partial longitudinal cross-sectional view of the probe according to FIG. 2 with the flexible cable assembly rotated 180°.

DETAILED DESCRIPTION

Figure 1:
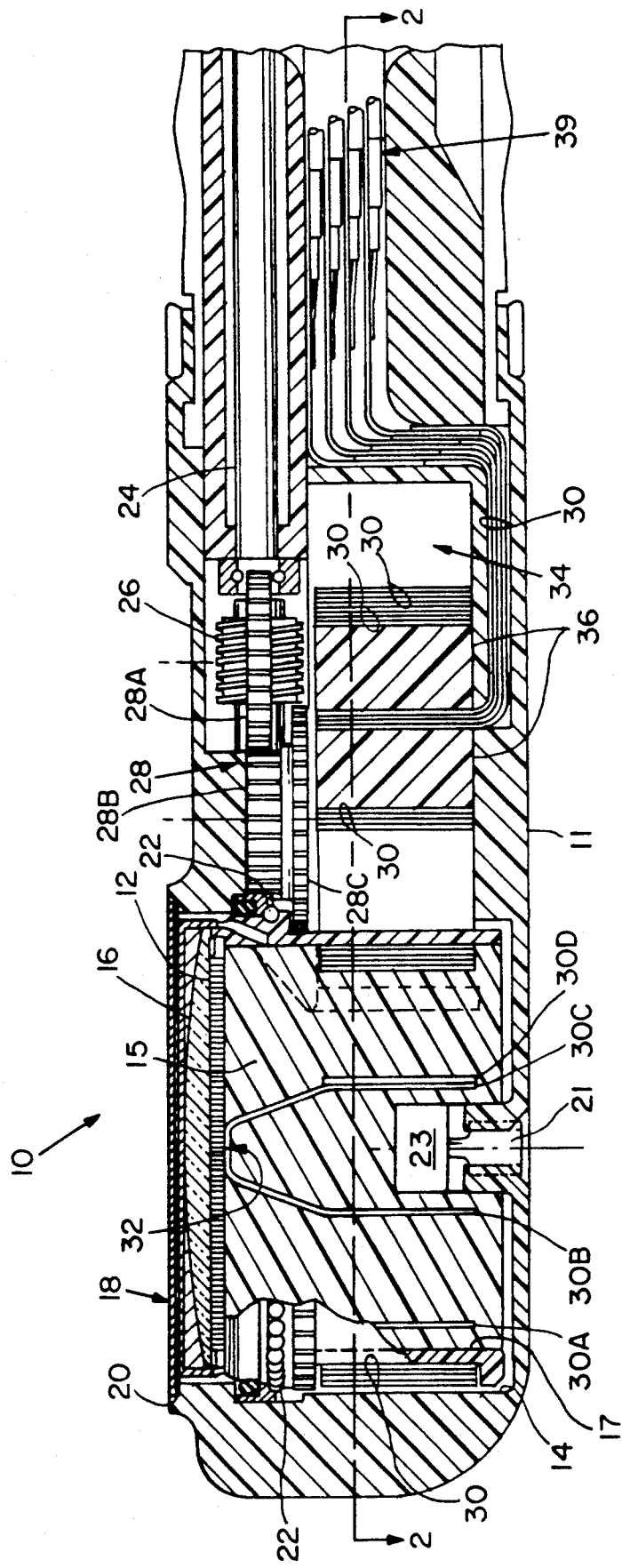
FIG. 1 is a longitudinal cross-sectional view of a portion of an ultrasound probe in accordance with the present invention.

A longitudinal cross-sectional view of an ultrasound probe illustrating the principles of the present invention is shown in FIG. 1. Preferably, a probe 10 is formed by modifying an endoscope whereby a rotatable ultrasound transducer array 12 is positioned in its distal end. As such, the probe 10 provides image data to remote electronics of an ultrasound imaging system which produces two-dimensional cross-sectional images of a subject. The probe 10 has a probe housing 11 shaped for insertion into a subject's esophagus. The rotatable ultrasound transducer array 12 comprises a plurality of elongated piezoelectric transducer elements arranged in a plane. The array is positioned on a support structure 17 within an inner volume 14 located at the distal end of the probe. Preferably, the transducer elements have different mechanical lengths such that the surface of the array 12 has a circular shape to provide maximum sensitivity.

A compound lens assembly 16 covering the rotatable array 12 serves to focus the energy emitted by the array along a plane which is parallel to the array elements. Additionally, this energy emitted from the array is electronically focused in a plane perpendicular to the plane of the array elements. A stationary cover assembly 18 is mounted over the inner housing 11 above the array. The cover prevents undesirable substances from touching the lens. A layer of grease 20, located between the lens assembly 16 and the cover 18, serves as a transmission medium.

The array is electrically connected to a flexible cable assembly 30 for communications with the remote ultrasound imaging electronics. More specifically, the flexible cable assembly extends from the array, through the inner volume 14 and a rear volume 34, to a plurality of individual conductors 39 adjacent to the rear volume which are coupled to the remote ultrasound electronics.

Figure 2:
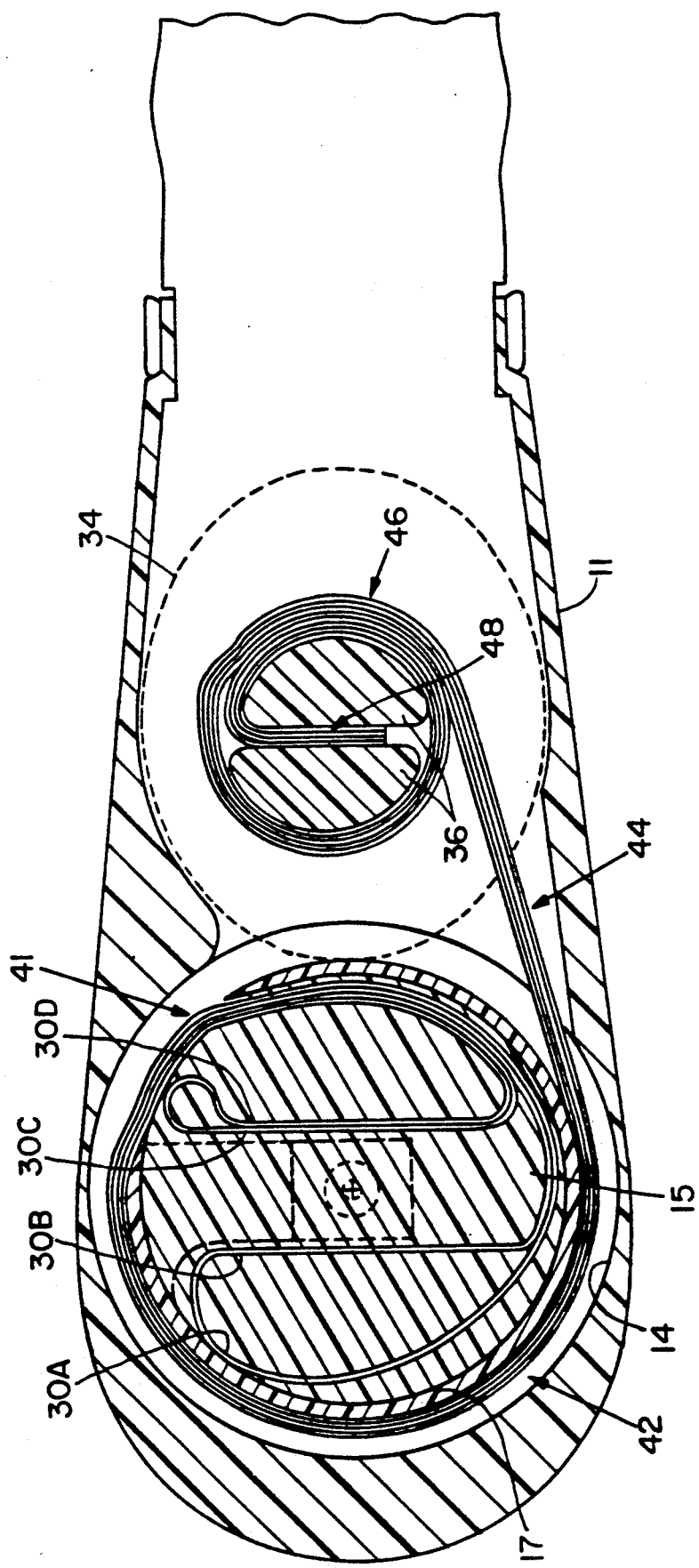
FIG. 2 is a partial longitudinal cross-sectional view of the probe of FIG. 1 taken along the line 2—2 of FIG. 1.

In one embodiment, the flexible cable assembly is a single flex cable comprising a plurality of individual flex cable extensions 30A-D, each having a plurality of signal lines printed thereon. Referring to FIG. 2, these individual flex cables are joined in pairs within the support structure, forming two unitary flex cables. Accordingly, flex cables 30A and 30B are integrally coupled as are flex cables 30C and 30D. Returning to FIG. 1, a common end of each flex cable pair is attached to the underside of the array at 32 forming a single flex cable. As shown in FIG. 2, the individual flex cables of the pairs extend in opposite directions, but flex cables 30A and 30D loop back becoming parallel to 30B and 30C within the support structure 17. A mass of acoustical damping material 15 fills the volume within support structure 17, encapsulating that portion of the individual flex cables. The acoustical damping material 15 absorbs acoustic signals from the back of the array.

The array 16 may be rotated about an axis extending through the center of the array and a shaft 21 for obtaining cross-sectional images along a variety of scan planes. The array is coupled to the rotatable support structure which is mechanically linked to a plurality of ball bearings 22 and to a bearing 23 at the shaft. Rotation of the array is achieved by a rotating cable 24 and a worm gear 26. More specifically, the rotating cable 24, resembling a speedometer cable, is mechanically linked to the worm gear 26. The rotation of the cable 24 causes the worm gear 26 to rotate about a common shaft. The worm gear is mechanically linked to a first gear 28A such that rotation of the worm gear causes the first gear to rotate about an axis which is parallel to the axis of rotation for the array. The first gear 28A is one of a plurality of gears 28 which are mechanically linked to each other and have parallel axes of rotation. Thus, the rotation of the worm gear drives the first gear 28A, the rotation of first gear drives the second gear 28B, the rotation of the second gear drives the third gear 28C. The third gear is mechanically linked to a ring gear 29 which is coupled to the support structure 17. Thus, the rotation of the third gear causes the ring gear to turn such that the array rotates.

The take-up mechanism comprising the flex cable assembly 30 in accordance with the present invention is shown in FIG. 2. As explained previously, the flex cable assembly has a first portion embedded within the mass of acoustical damping material 15. The flex cable assembly protrudes out of the damping material through an opening in the support structure at 41 and extends around the support structure within the inner volume in the form of a loop 42. The loop portion 42 becomes straight at 44 and extends into the rear volume 34. The flex cable assembly is formed into a spiral portion 46 which is wrapped around a stationary attachment means 36 within the rear volume 34. The attachment means preferably comprises a clamp, though any functionally similar device may be employed. The spiral portion has a sufficient number of revolutions of excess cable to support rotation of the array. An innermost section 48 of the spiral portion is fixed within the clamp. Also, the innermost section 48 is coupled to the individual conductors 39 (FIG. 1) which are electrically linked to the remote imaging electronics.

As the array rotates, the rotating support structure causes the damping material along with the embedded portion of the flex cable assembly to rotate with it. This rotation causes the loop portion 42 to rotate, thereby changing the amount of cable forming the loop portion 42 which surrounds the damping material 15. Such changes cause corresponding changes in the amount of cable forming the spiral portion as well as changes in the diameter of the spiral portion. For example, as shown in FIG. 2, clockwise rotation of the array increases the amount of cable forming the loop portion. Accordingly, an increase in the amount of cable forming the loop portion causes a decrease in the amount of cable forming the spiral portion and in the diameter of the spiral portion. An example of counterclockwise rotation of the array is shown in FIG. 3. In this situation, the rotation of the array has significantly reduced the amount of cable form the loop portion. As such, the amount of cable forming the spiral portion and the outer diameter of the spiral portion have increased.

The take-up mechanism of this invention comprising flex cable assembly is configured to minimize the required diameter of the inner volume 14. As such, the probe has a smaller transverse cross-sectional area and is easier to swallow. More specifically, the present invention has the loop portion 42 within the inner volume 14 driving a spiral portion 46 located in a rear volume 34. The rotation of the array causes the loop portion to form, at most, one complete revolution within the inner housing, and that single revolution is wrapped somewhat tightly against the support structure. Accordingly, the thickness of the loop portion of the flex cable assembly within the inner volume is minimized.

The spiral portion rotates in response to the loop portion and has a sufficient amount of cable to support rotation of the array. The spiral portion 46 is positioned in the rear volume 34 and actually has a smaller transverse cross-sectional diameter than the loop portion. Referring to FIG. 3, this smaller diameter is achieved based on two reasons explained herein. The spiral portion is wrapped around the clamp 36 such that the inner diameter of the spiral is smaller than the loop diameter. Thus, the spiral portion can "take-up" multiple revolutions of cable from the loop portion and still maintain a smaller outer diameter (i.e. transverse cross-sectional outer diameter) than the loop portion. Additionally, the elongated shape of the rear volume 34 has a sufficient volume to accommodate multiple revolutions of the spiral portion even when it becomes slack. While this invention has been particularly shown and described above with references to specific embodiments, the foregoing and other changes in form and detail may be made by one skilled in the art without departing from the spirit and scope of the invention. Accordingly, the take-up mechanism may comprise other forms of the flexible cable such as an "S" shaped cable configuration. Also, while the present invention is employed in a probe having a transducer array, the probe may comprise a mechanical scanner without departing from the scope of the present invention.

I claim:

1. An endoscopic ultrasound probe comprising:
    a probe housing;
    means defining a first volume within the probe housing supporting a rotatable transducer assembly which is adapted to be rotated relative to the probe housing about an axis of rotation extending through the assembly and the first volume; and
    means defining a second volume within the probe housing, the second volume being adjacent to the first volume and being spaced apart from the axis of rotation of the assembly;
    a take-up mechanism located in the second volume comprising a flexible cable disposed within the second volume and connected to the transducer assembly in the first volume, the take-up mechanism being responsive to the rotating array in changing the amount of the flexible cable within the second volume corresponding to changes in the amount of flexible cable within the first volume produced by the rotating array.

2. An endoscopic ultrasound probe as claimed in claim 1 in which the flexible cable comprises a plurality of flex cables, each flex cable comprising a printed circuit having a plurality of signal lines located thereon.

3. An endoscopic ultrasound probe as claimed in claim 1 wherein the amount of flexible cable within the first volume is less than the amount of flexible cable within the second volume.

4. An endoscopic ultrasound probe for use with an ultrasound imaging system comprising:
    a probe housing;
    means defining an inner volume within the probe housing;
    a rotatable transducer array supported within the inner volume, the array adapted to be rotated relative to the probe housing about an axis of rotation extending through the array and into the inner volume,
    means defining a rear volume within the probe housing, the rear volume being adjacent to the inner volume spaced apart from the axis of rotation of the array; and
    a take-up mechanism comprising a flexible cable for electrically connecting the array to ultrasound imaging system electronics, the cable being attached to the array and having a first portion within the inner volume, the cable further extending from the inner volume into the rear volume, the cable having a second portion in the form of a spiral of variable diameter within the rear volume, the cable having a fixing section within the spiral, the fixed section being coupled to the remote ultrasound electronics.

5. An endoscopic ultrasound probe as claimed in claim 4 in which the flexible cable comprises a plurality of flex cables, each flex cable comprising a printed circuit having a plurality of signal lines located thereon.

6. An endoscopic ultrasound probe for use with remote ultrasound electronics in two-dimensional transesophageal echo cardiography comprising:
    a probe housing;
    means defining an inner volume within a distal end of the probe housing;
    a rotatable transducer array supported within the inner volume, the array having a scan plane which is perpendicular to a plane of the array, the array being adapted to be rotated relative to the probe housing about an axis of rotation extending through the array and into the inner volume, the axis of rotation being substantially perpendicular to the plane of the array;
    means defining a rear volume within the probe housing, the rear volume being adjacent to the inner volume and spaced apart from the axis of rotation of the array;
    an attachment means located within the rear volume; and
    a flex cable assembly for electrically connecting the array to the remote ultrasound electronics, the flex cable assembly having one end attached to the array, the flex cable assembly having a loop portion disposed within the inner volume, the loop portion of flex cable assembly extending from the inner volume into the rear volume, the flex cable assembly having a spiral portion of variable diameter within the rear volume, the spiral portion having an innermost section fixed by the attachment means, the fixed section of the spiral portion being coupled to the remote ultrasound electronics, wherein the amount of the flex cable assembly comprising the loop portion changes as the array rotates producing corresponding changes in the amount of the flex cable assembly comprising the spiral portion, wherein said corresponding changes in the amount of the flex cable assembly comprising the spiral portion produce changes in the diameter of the spiral portion.

7. An endoscopic ultrasound probe as claimed in claim 6 wherein the flex cable assembly comprises a plurality of flex cables, each flex cable comprising a printed circuit having a plurality of signal lines.

8. An endoscopic ultrasound probe as claimed in claim 6 wherein the attachment means comprises a clamp.

* * * * *